US00PP32317P2

(12) United States Plant Patent
Wood

(10) Patent No.: US PP32,317 P2
(45) Date of Patent: Oct. 13, 2020

(54) ***HYDRANGEA* PLANT NAMED 'SMNHML'**

(50) Latin Name: *Hydrangea macrophylla*
Varietal Denomination: SMNHML

(71) Applicant: Spring Meadow Nursery, Inc., Grand Haven, MI (US)

(72) Inventor: Timothy D Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 16/602,723

(22) Filed: Nov. 26, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./227, 250
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Hydrangea* plant named 'SMNHML' is disclosed, characterized by vibrant flower colors on very upright plants with strong stems. Plants blue well in acidic soil conditions. The new variety is a *Hydrangea*, normally produced as an ornamental plant.

3 Drawing Sheets

Latin name of the genus and species: *Hydrangea macrophylla.*

Variety denomination: 'SMNHML'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with new, colors, hardiness, strong stems, and large panicles. The cross resulting in this new variety was made during 2011.

The seed parent is the variety *Hydrangea macrophylla* 'SMNHMSIGMA', U.S. Plant Pat. No. 26,929. The pollen parent is the variety *Hydrangea macrophylla* 'Paris Rapa', U.S. Plant Pat. No. 10,906. The new variety was identified as a potentially interesting selection in the Summer of 2015, at a commercial greenhouse in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'SMNHML' by vegetative softwood cuttings was first performed during the Summer of 2015, at a commercial greenhouse in Grand Haven, Mich. Subsequent propagation has shown that the unique features of this cultivar are stable and reproduced true to type in 2 successive generations.

SUMMARY OF THE INVENTION

The cultivar 'SMNHML' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHML' These characteristics in combination distinguish 'SMNHML' as a new and distinct *Hydrangea* cultivar:

1. Vibrant flower colors.
2. Very upright plant form.
3. Strong stems.
3. Blues well with changing soil pH.

PARENT COMPARISONS

Plants of the new cultivar 'SMNHML' are similar to plants of the seed parent in most horticultural characteristics, however, plants of the new cultivar 'SMNHML' differ in the following;

1. The new variety and seed parent both have red sepals.
2. The new variety has larger sepals than the seed parent.
3. The new variety blues easily with acidic soil, while the seed parent does not.

Plants of the new cultivar 'SMNHML' are similar to plants of the pollen parent in most horticultural characteristics, however, plants of the new cultivar 'SMNHML' differ in the following;

1. The new variety has darker pink sepals than the pollen parent.
2. The new has larger panicles than the pollen parent.
3. The new variety has larger sepals than the pollen parent.

COMMERCIAL COMPARISON

Plants of the new cultivar 'SMNHML' can be compared to the variety *Hydrangea* 'Red Sensation', U.S. Plant Pat.

No. 18,197. These varieties are similar in most horticultural characteristics; however 'SMNHML' differs in the following:

1. The new variety has larger sepals than this comparator.

BRIEF DESCRIPTION OF THE PHOTOGRAPHS

'SMNHML' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new *Hydrangea*.

DETAILED BOTANICAL DESCRIPTION

Figure 1:
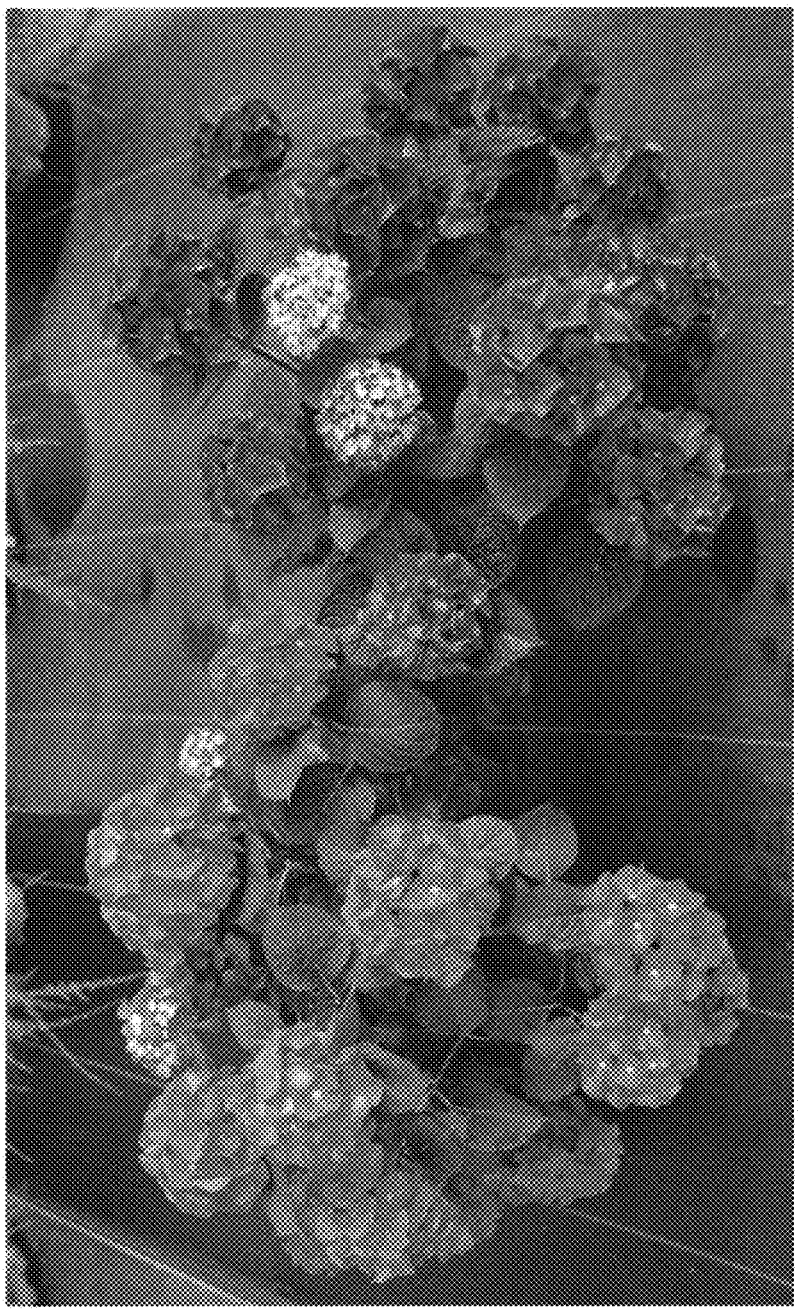
FIG. 1 shows two plants of 'SMNHML' grown in Grand Haven, Mich. at the age of approximately 18 months. The plant on the right has been given a typical commercial aluminum treatment to cause bluing.
Figure 2:
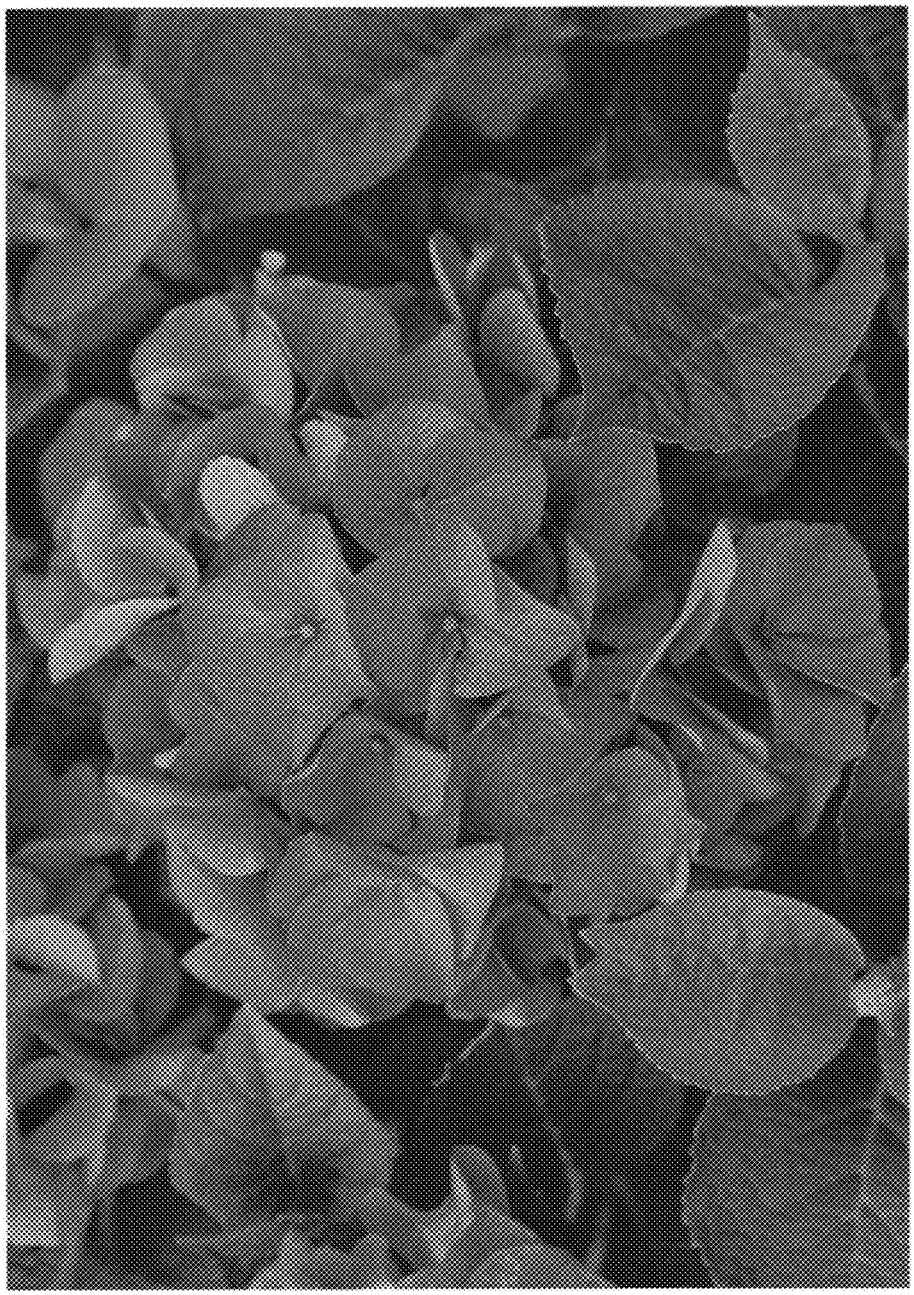
FIG. 2 shows a close-up view of the mature inflorescence during late Summer given a typical commercial aluminum treatment to cause bluing.
Figure 3:
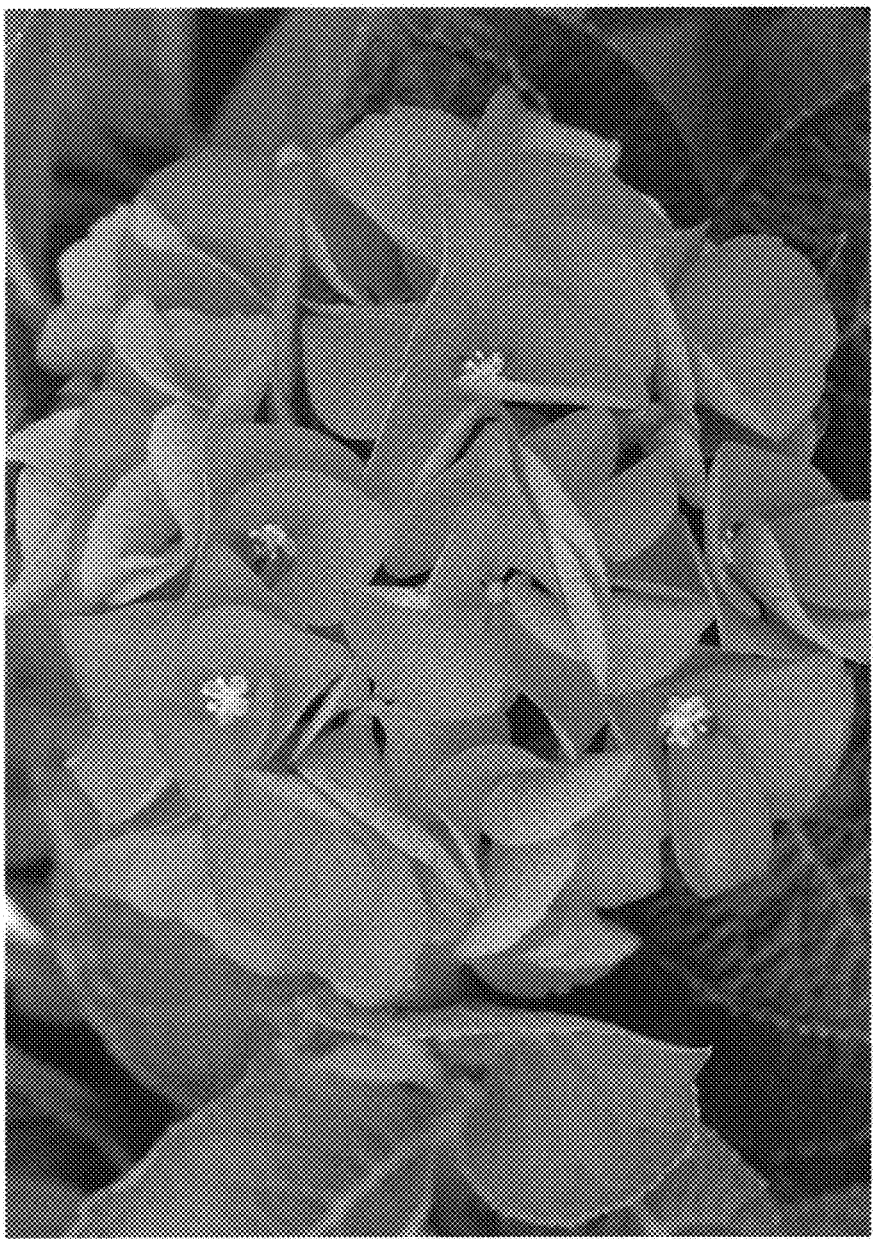
FIG. 3 shows a close-up view of the mature inflorescence during late Summer on a plant not given aluminum treatment.

In the following description, color references are made to The Royal Horticultural Society Color Chart 2015 except where general terms of ordinary dictionary significance are used. The following observations and measurements describe 'SMNHML' plants grown in a commercial poly greenhouse in Grand Haven, Mich. under natural lighting. Measurements were taken during Summer of 2017. The plants were about 3 years old planted in the ground. The growing temperature ranged from 5° C. to 27° C. Measurements and numerical values represent averages of typical plant types.

Botanical classification: *Hydrangea macrophylla* 'SMNHML'.

PROPAGATION

Time to initiate roots: Approximately 18 days.
Time to produce a rooted young plants: Approximately 60 days.
Propagation method: Softwood cuttings.
Roots: Thick, fine, fibrous, moderately dense. White and brown in color, not accurately measured with R.H.S. chart.

PLANT

Plant type: Flowering deciduous perennial shrub.
Age of plant described: Approximately 2 to 3 years old.
Growth habit: Upward and outward.
Overall plant shape: Rounded.
Height: 43 cm.
Spread: 88 cm.
Growth rate: Good.
Plant vigor: Moderate.
Branching habit: Upward and outward, some drooping over.
Length of primary lateral branches: 42 cm.
Diameter of lateral branches: 8 mm.
Quantity of lateral branches: About 15.

Stem:
- *Stem shape*.—Round with lenticels.
- *Stem strength*.—Good.
- *Color*.—Immature: RHS Green 143C. Mature: RHS Green 143C.
- *Pubescence*.—None.
- *Aspect*.—15 to 80°.

Internode length: 5 cm.
Lenticels: Colored RHS Purple 79A.

FOLIAGE

Leaf:
- *Arrangement*.—Opposite.
- *Leaf shape*.—Ovate.
- *Average length*.—6 cm.
- *Average width*.—2.5 cm.
- *Apex*.—Acute to acuminate.
- *Base*.—Cuneate.
- *Margin*.—Serrate.
- *Texture of top surface*.—Smooth, leathery.
- *Texture of bottom surface*.—Smooth, ribbed.
- *Leaf pubescence*.—None.
- *Color*.—Young foliage upper side: RHS Green 141A. Young foliage under side: RHS Green 139C. Mature foliage upper side: RHS Green 141A. Mature foliage under side: RHS Green 139C.
- *Venation*.—Pattern: Pinnate. Color upper side: RHS Yellow-Green 144C. Color under side: RHS Yellow-Green 144D.
- *Petiole*.—Average Length: 2 cm. Diameter: 4 mm. Petiole color upper side: RHS Yellow-Green 144C. Petiole color lower side: RHS Yellow-Green 144C. Petiole Texture upper side: Smooth, some pubescence. Petiole Texture lower side: Smooth.

FLOWER

Natural flowering season: Early to late Summer.
Inflorescence:
- *Type*.—Mophead.
- *Quantity of flowers per inflorescence*.—Fertile flowers: 15-20. Sterile flowers: Over 100.
- *Persistent or self-cleaning*.—Self-cleaning.
- *Fragrance*.—None detected.

Panicle:
- *Shape*.—Round, orbital.
- *Height*.—11 cm.
- *Diameter*.—17 cm.

Sterile flower:
- *Bud shape*.—Obovate.
- *Bud length*.—2 mm.
- *Bud diameter*.—2 mm.
- *Bud color*.—Acidic: RHS Blue 105C. Basic: RHS Red-Purple 73B.
- *Flower aspect*.—Upright and outward.
- *Flower length*.—9 mm.
- *Flower diameter*.—1.5 mm.
- *Persistence*.—Self-cleaning.

Sterile flower petals:
- *Petal arrangement*.—Whorl, cruciform.
- *Quantity*.—4.
- *Length of petal*.—3.25 mm.
- *Width of petal*.—2 mm.
- *Apex*.—Acute.
- *Shape of petal*.—Ovate.

*Petal margin*.—Entire.
*Petal base*.—Cuneate.
*Petal texture*.—Smooth, upper and under side.
*Color*.—Upper surface at first opening: Acidic: RHS Blue 104B. Basic: RHS Red-Purple 65A. Under surface at first opening: Acidic: RHS Blue 104B. Basic: RHS Red-Purple 65A. Upper surface at maturity: Acidic: RHS Blue 104B. Basic: RHS Red-Purple 65A. Under surface at maturity: Acidic: RHS Blue 104B. Basic: RHS Red-Purple 65A.

Sterile flower sepal:
*Arrangement*.—Whorl, overlapping.
*Number*.—4.
*Shape*.—Ovate.
*Tip*.—Acute.
*Base*.—Obtuse.
*Margin*.—Entire.
*Length*.—2 cm.
*Width*.—2 cm.
*Texture, upper*.—Smooth, waxy.
*Texture, lower*.—Smooth.
*Color*.—Upper surface at first opening: Acidic: Mix of RHS Purple NN75A and Blue 99D. Basic: RHS Red-Purple 67A. Under surface at first opening: Acidic: Mix of RHS Purple NN75A and Blue 99D. Basic: RHS Red-Purple 67A. Upper surface at maturity: Acidic: Mix of RHS Purple NN75A and Blue 99D. Basic: RHS Red-Purple 67A. Under surface at maturity: Acidic: Mix of RHS Purple NN75A and Blue 99D. Basic: RHS Red-Purple 67A. Upper surface, fading: Acidic: Mostly RHS Blue N95B with some Purple-Violet N80B. Basic: RHS Red-Purple 68A, less saturated color. Under surface, fading: Acidic: Mostly RHS Blue N95B with some Purple-Violet N80B. Basic: RHS Red-Purple 68A, less saturated color.

Sterile flower pedicel:
*Length*.—2 cm.
*Diameter*.—1.5 mm.
*Angle*.—45°.
*Strength*.—Good.
*Texture*.—Smooth, pubescent.
*Color*.—Acidic: RHS Blue N95C. Basic: RHS Red-Purple 67C.

Fertile flower:
*Bud shape*.—Obovate.
*Bud length*.—3 mm.
*Bud diameter*.—3 mm.
*Bud color*.—RHS Yellow-Green 145B to: Acidic: RHS Blue group 104D. Basic: RHS Red-Purple 73C.
*Flower aspect*.—Upright and outward.
*Flower shape*.—Star-like.
*Flower diameter*.—2.8 cm.
*Flower length*.—2.6 cm.
*Flower depth*.—2.2 mm.
*Persistence*.—Self-cleaning.

Fertile flower petals:
*Arrangement*.—Whorl.
*Quantity*.—5.
*Length of petal*.—5 mm.
*Width of petal*.—2 mm.
*Apex*.—Acute.
*Shape of petal*.—Ovate.
*Petal margin*.—Entire.
*Petal base*.—Cuneate.
*Petal texture*.—Smooth, upper and under side.
*Color*.—Upper surface at first opening: Acidic: RHS Blue 104B. Basic: RHS Red-Purple 65A. Under surface at first opening: Acidic: RHS Blue 104B. Basic: RHS Red-Purple 65A. Upper surface at maturity: Acidic: RHS Blue 104B. Basic: RHS Red-Purple 65A. Under surface at maturity: Acidic: RHS Blue 104B. Basic: RHS Red-Purple 65A.

Fertile flower sepal: Inconspicuous.

Fertile flower pedicel:
*Angle*.—45°.
*Strength*.—Good.
*Length*.—5 mm.
*Width*.—1 mm.
*Texture*.—Smooth, some pubescence.
*Color*.—Acidic: RHS Blue N95C. Basic: RHS Red-Purple 67C.

REPRODUCTIVE ORGANS

Sterile flowers:
Stamens:
*Number*.—7.
*Filament length*.—2 mm.
*Filament color*.—RHS Green-White 157D.
Anthers:
*Shape*.—Round.
*Length*.—1 mm.
*Color*.—RHS Green-White 157D.
*Pollen color*.—RHS Green-White 157D.
*Pollen amount*.—Some.
Pistil:
*Number*.—1.
*Length*.—1 mm.
*Style*.—Length: 0.5 mm. Color: RHS Green-White 157D. Ovary color: Too minute to measure accurately.
*Stigma*.—Shape: Lobed. Color: Acidic: RHS Violet-Purple 98B. Basic: RHS Red-Purple 68B.

Fertile flowers:
Stamens:
*Number*.—8-10.
*Filament length*.—1.1 cm.
*Filament color*.—RHS White NN155C.
Anthers:
*Shape*.—Round.
*Length*.—1.5 mm.
*Color*.—RHS Green-White 157A.
*Pollen color*.—RHS Green-White 157A.
*Pollen amount*.—Some.
Pistil:
*Number*.—1, 2-lobed.
*Length*.—1 mm.
*Style*.—Length: 0.5 mm. Color: Acidic: RHS Blue 106B. Basic: RHS White N155B. Ovary color: Too minute to measure accurately.
*Stigma*.—Shape: Oblong. Color: Acidic: RHS Blue 106B. Basic: RHS White N155B.

OTHER CHARACTERISTICS

Seeds and fruits: None observed.
Disease/pest resistance: Neither resistance nor susceptibility to normal diseases and pests of *Hydrangea* have been observed.
Temperature tolerance: USDA Zones 4 to 9.

What is claimed is:

1. A new and distinct cultivar of *Hydrangea* plant named 'SMNHML' as herein illustrated and described.

* * * * *